US 8,419,763 B2

(12) United States Patent
Nikolchev et al.

(10) Patent No.: US 8,419,763 B2
(45) Date of Patent: Apr. 16, 2013

(54) SAFETY NEEDLE FOR ACCESSING THE INTERIOR OF A HIP JOINT

(75) Inventors: Julian Nikolchev, Portola Valley, CA (US); Chris Pamichev, Sunnyvale, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 1109 days.

(21) Appl. No.: 12/210,584

(22) Filed: Sep. 15, 2008

(65) Prior Publication Data
US 2009/0182340 A1 Jul. 16, 2009

Related U.S. Application Data

(60) Provisional application No. 60/993,615, filed on Sep. 13, 2007.

(51) Int. Cl.
*A61B 17/34* (2006.01)
*A61F 2/46* (2006.01)
*A61M 5/178* (2006.01)

(52) U.S. Cl.
USPC .................. 606/185; 604/158; 606/86 R

(58) Field of Classification Search ............... 606/86 R, 606/185; 604/158
See application file for complete search history.

(56) References Cited

U.S. PATENT DOCUMENTS

| 2,623,521 A | * | 12/1952 | Shaw ................. 604/170.02 |
|---|---|---|---|
| 4,379,458 A | | 4/1983 | Bauer et al. |
| 4,464,169 A | | 8/1984 | Semm |
| 4,535,773 A | | 8/1985 | Yoon |
| 4,601,710 A | | 7/1986 | Moll |
| 4,654,030 A | | 3/1987 | Moll et al. |
| 4,769,018 A | | 9/1988 | Wilson |
| 4,808,168 A | | 2/1989 | Warring |
| 4,869,717 A | | 9/1989 | Adair |
| 4,874,362 A | | 10/1989 | Wiest et al. |
| 4,902,280 A | | 2/1990 | Lander |
| 4,931,042 A | | 6/1990 | Holmes et al. |
| 5,013,294 A | | 5/1991 | Baier |
| 5,098,388 A | | 3/1992 | Kulkashi et al. |
| 5,125,553 A | | 6/1992 | Oddsen et al. |
| 5,139,478 A | | 8/1992 | Koninckx et al. |
| 5,209,721 A | | 5/1993 | Wilk |
| 5,261,891 A | * | 11/1993 | Brinkerhoff et al. .... 604/164.12 |
| 5,295,993 A | | 3/1994 | Green |
| 5,312,363 A | | 5/1994 | Ryan et al. |
| 5,330,488 A | | 7/1994 | Goldrath |

(Continued)

FOREIGN PATENT DOCUMENTS

DE   10 2006 024 757   *   5/2006

*Primary Examiner* — Kevin T Truong
*Assistant Examiner* — David Bates
(74) *Attorney, Agent, or Firm* — Pandiscio & Pandiscio

(57) ABSTRACT

A safety needle comprising a handle; a hollow needle; a trigger carriage; an obturator; a spring; a trigger; a first latch and a second latch; the first latch, second latch and trigger being configured so that when the trigger carriage is in a distal position and the first latch set, and the trigger is thereafter pulled proximally, the first latch is released and the trigger carriage moves proximally into a proximal position, and thereafter releasing the trigger causes the trigger carriage to move into an intermediate position and set the second latch; and further wherein, when the trigger carriage is in its intermediate position and the distal end of the obturator engages tissue, the trigger carriage is moved proximally so as to release the second latch.

17 Claims, 28 Drawing Sheets

U.S. PATENT DOCUMENTS

| | | | |
|---|---|---|---|
| 5,389,077 A | 2/1995 | Melinyshyn et al. | |
| 5,421,821 A | 6/1995 | Janicki et al. | |
| 5,431,666 A | 7/1995 | Sauer et al. | |
| 5,478,329 A | 12/1995 | Ternamian | |
| 5,486,190 A | 1/1996 | Green | |
| 5,501,691 A | 3/1996 | Goldrath | |
| 5,549,565 A | 8/1996 | Ryan et al. | |
| 5,569,161 A | 10/1996 | Ebling et al. | |
| 5,569,205 A | 10/1996 | Hart et al. | |
| 5,578,053 A * | 11/1996 | Yoon | 606/185 |
| 5,593,420 A | 1/1997 | Eubanks, Jr. et al. | |
| 5,630,805 A | 5/1997 | Ternamian | |
| 5,643,301 A | 7/1997 | Mollenauer | |
| 5,645,076 A | 7/1997 | Yoon | |
| 5,645,557 A | 7/1997 | Yoon | |
| 5,665,102 A | 9/1997 | Yoon | |
| 5,669,883 A | 9/1997 | Scarfone et al. | |
| 5,676,156 A | 10/1997 | Yoon | |
| 5,693,031 A | 12/1997 | Ryan et al. | |
| 5,695,462 A | 12/1997 | Sutcu et al. | |
| 5,707,362 A | 1/1998 | Yoon | |
| 5,800,381 A | 9/1998 | Ognier | |
| 5,800,394 A | 9/1998 | Yoon et al. | |
| 5,823,947 A | 10/1998 | Yoon et al. | |
| 5,827,315 A | 10/1998 | Yoon | |
| 5,842,971 A | 12/1998 | Yoon | |
| 5,871,471 A | 2/1999 | Ryan et al. | |
| 5,882,340 A | 3/1999 | Yoon | |
| 5,893,874 A | 4/1999 | Bourque et al. | |
| 5,899,919 A | 5/1999 | Eubanks, Jr. et al. | |
| 6,007,561 A | 12/1999 | Bourque et al. | |
| 6,099,505 A | 8/2000 | Ryan et al. | |
| 6,120,437 A | 9/2000 | Yoon et al. | |
| 6,146,401 A | 11/2000 | Yoon et al. | |
| 6,162,196 A | 12/2000 | Hart et al. | |
| 6,193,692 B1 | 2/2001 | Harris et al. | |
| 6,217,555 B1 | 4/2001 | Hart et al. | |
| 6,235,037 B1 | 5/2001 | East et al. | |
| 6,238,373 B1 | 5/2001 | de la Torre et al. | |
| 6,270,484 B1 | 8/2001 | Yoon | |
| 6,299,592 B1 | 10/2001 | Zander | |
| 6,309,397 B1 | 10/2001 | Julian et al. | |
| 6,364,827 B1 | 4/2002 | Irion et al. | |
| 6,402,714 B1 | 6/2002 | Kraft-Kivikoski | |
| 6,497,716 B1 | 12/2002 | Green et al. | |
| 6,544,231 B1 | 4/2003 | Palmer et al. | |
| 6,546,787 B1 | 4/2003 | Schiller et al. | |
| 6,603,997 B2 | 8/2003 | Doody | |
| 6,632,194 B1 | 10/2003 | Mehner et al. | |
| 6,656,160 B1 | 12/2003 | Johnson et al. | |
| 6,723,709 B1 | 4/2004 | Pressato et al. | |
| 6,840,935 B2 | 1/2005 | Lee | |
| 6,905,489 B2 * | 6/2005 | Mantell et al. | 604/506 |
| 6,916,331 B2 | 7/2005 | Mollenauer et al. | |
| 7,001,363 B2 | 2/2006 | Ferguson et al. | |
| 7,029,461 B2 | 4/2006 | Ferguson et al. | |
| 7,037,292 B2 | 5/2006 | Carlyon | |
| 7,125,403 B2 | 10/2006 | Julian et al. | |
| 7,169,159 B2 | 1/2007 | Green et al. | |
| 8,057,502 B2 * | 11/2011 | Maliglowka et al. | 606/185 |

* cited by examiner

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

SAFETY NEEDLE FOR ACCESSING THE INTERIOR OF A HIP JOINT

REFERENCE TO PENDING PRIOR PATENT APPLICATION

This patent application claims benefit of prior U.S. Provisional Patent Application Ser. No. 60/993,615, filed Sep. 13, 2007 by Julian Nikolchev et al. for SAFETY NEEDLE FOR ACCESSING THE INTERIOR OF A HIP JOINT, which patent application is hereby incorporated herein by reference.

FIELD OF THE INVENTION

This invention relates to surgical methods and apparatus in general, and more particularly to methods and apparatus for treating the hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D. With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the femur and the hip. More particularly, and looking now at FIG. 2, the ball of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure around the age of 25 or so) so as to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIG. 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See FIGS. 11 and 12.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as a cam-type femoroacetabular impingement (i.e., a cam-type FAI). In other cases, and looking now at FIG. 14, the impingement can occur due to irregularities in the geometry of the acetabular cup. This latter type of impingement is sometimes referred to as a pincer-type femoroacetabular impingement (i.e., a pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to the patient's tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively spacious when compared to the hip joint. As a result, it is relatively difficult for surgeons to perform minimally-invasive procedures on the hip joint.

Furthermore, the pathways for entering the interior of the hip joint (i.e., the pathways which exist between adjacent bones) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is set at approximately a right angle to the angle of re-attachment. This makes drilling into bone, for example, much more complicated than where the angle of approach is effectively aligned with the angle of re-attachment, such as is frequently the case in the shoulder joint. Furthermore, the working space within the hip joint is typically extremely limited, further complicating repairs where the angle of approach is not aligned with the angle of re-attachment.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Arthroscopic Access to the Interior of the Hip Joint

Successful hip arthroscopy generally requires safe and reliable access to the interior of the hip joint. More particularly, successful hip arthroscopy generally requires the creation of a plurality of access portals which extend from the surface of the skin, through the underlying muscle tissue, through the capsule of the joint, and then down to the specific surgical site within the interior of the hip joint. Depending on the specific surgical site which is to be accessed within the interior of the hip joint, different anatomical pathways may be utilized for the access portals. By way of example but not limitation, one anatomical pathway may be used where a torn labrum is to be repaired, and another anatomical pathway may be used where the lesser trochanter must be addressed. And, in most cases, multiple access portals are generally required, with one access portal being used for visualization (i.e., to deploy an arthroscope), another access portal being used for irrigation, another access portal being used to pass surgical instruments to and from the surgical site, etc.

However, the creation of access portals can be problematic. For one thing, the patient's anatomy (e.g., bone, blood vessels, nerves, etc.) can greatly restrict the possible portal locations. Furthermore, some hip structures (e.g., the articular cartilage on the femoral head, the articular cartilage on the acetabular cup, etc.) can be quite delicate, thereby requiring great precision when forming the access portal so as to avoid damaging delicate structures. Additionally, some of the intervening tissue (e.g., the joint capsule) can be quite tough, thus requiring substantial force to penetrate the tissue, and thereby raising the danger of accidental plunging as an access tool "breaks through" the intervening tissue. Such accidental plunging increases the risk of inadvertently damaging delicate joint structures (e.g. articular cartilage) located on the far side of the intervening tissue.

Due to the numerous difficulties and concerns associated with forming an access portal, surgeons have traditionally resorted to a multi-step procedure for forming an access portal.

More particularly, surgeons have traditionally first passed a small needle (sometimes referred to as an access needle) down to the interior of the hip joint. This is generally done by first using external anatomical landmarks and tactile feedback for needle guidance; then, as the sharp tip of the access needle enters the capsule of the joint and approaches delicate structures (e.g. articular cartilage), fluoroscopy is used to carefully direct final needle placement. Inexperienced surgeons, or experienced surgeons dealing with particularly problematic cases, may also use fluoroscopy during the earlier stages of needle placement.

Once the access needle has been positioned, the tissue surrounding the access needle is opened laterally by passing a series of tissue dilators over the access needle. These tissue dilators progressively increase in diameter so as to dilate the intervening tissue disposed between the skin and the interior of the joint.

After the intervening tissue has been laterally dilated, a tubular liner (sometimes referred to as an access cannula) is inserted over the access needle. This access cannula holds the incision open and provides a surgical pathway down to the interior of the hip joint, thereby enabling keyhole surgery to be performed on the hip joint.

Once the access cannula has been emplaced, the access needle may be withdrawn, leaving the full diameter of the access cannula available for passing instruments and the like down to the surgical site. Alternatively, in many cases, the access needle may be left in place and thereafter used as a guidewire for directing instruments down to the surgical site.

The Need for an Improved Access Needle

As noted above, arthroscopic access to the interior of the hip joint generally requires the creation of an access portal into the interior of the hip joint and, as further noted above, the creation of an access portal into the interior of the hip joint in turn typically requires passing an access needle from the surface of the skin down to the interior of the hip joint. Due to the sharpness of the access needle and the delicate structures of the hip joint, passing the access needle down to the interior of the hip joint is often an anxious and time-consuming procedure for the surgeon, even where fluoroscopy is used, and even where the surgeon is experienced. By way of example but not limitation, there is considerable concern as the needle is passed through the capsule. This is because high push forces are needed to penetrate through the tough fibers of the capsule, but the delicate articular cartilage of the femoral head and/or the acetabular cup lie just beneath the capsule, so any uncontrolled plunging of the access needle can cause serious injury to the patient's anatomy. As a result of these concerns, needle placement typically proceeds relatively slowly, even with experienced surgeons, and there is typically substantial use of fluoroscopy during needle placement. Such use of fluoroscopy during needle placement tends to slow down the procedure and exposes the patient to additional radiation.

On account of the foregoing, there is a substantial need for a safer and more convenient approach for creating an access portal to the interior of the hip joint.

More particularly there is a substantial need for a new safety needle for accessing the interior of the hip joint.

SUMMARY OF THE INVENTION

The present invention provides a safer and more convenient approach for creating an access portal to the interior of the hip joint.

More particularly, the present invention comprises the provision and use of a novel safety needle for accessing the interior of the hip joint. This safety needle provides a safer, more controlled and more convenient approach for creating access to the interior of the hip joint.

In one preferred form of the invention, there is provided a safety needle comprising:
a handle;
a hollow needle mounted to the handle, the hollow needle having a sharp distal end;
a trigger carriage slidably mounted to the handle for movement between a distal position and a proximal position;
an obturator mounted to the trigger carriage and slidably received within the hollow needle, the obturator having a distal end, and the obturator being sized such that (i) when the trigger carriage is in its distal position, the distal end of the obturator extends beyond the distal end of the needle, and (ii) when the trigger carriage is in its proximal position, the distal end of the obturator is received within the distal end of the needle;
a spring for urging the trigger carriage into its distal position;
a trigger mounted to the trigger carriage for urging the trigger carriage towards its proximal position;
a first latch for releasably locking the trigger carriage in its distal position;
a second latch for releasably locking the trigger carriage in an intermediate position located between the distal position and the proximal position, wherein the distal end of the obturator partially emerges from the hollow needle;
the first latch, second latch and trigger being configured so that when the trigger carriage is in its distal position and the first latch set, and the trigger is thereafter pulled proximally, the first latch is released and the trigger carriage moves proximally into its proximal position, and thereafter releasing the trigger causes the trigger carriage to move into its intermediate position and set the second latch;
and further wherein, when the trigger carriage is in its intermediate position and the distal end of the obturator engages tissue, the trigger carriage is moved proximally so as to release the second latch.

In another form of the present invention, there is provided a method for accessing the interior of a hip joint, the method comprising:
providing a safety needle comprising:
a handle;
a hollow needle mounted to the handle, the hollow needle having a sharp distal end;
a trigger carriage slidably mounted to the handle for movement between a distal position and a proximal position;
an obturator mounted to the trigger carriage and slidably received within the hollow needle, the obturator having a distal end, and the obturator being sized such that (i) when the trigger carriage is in its distal position, the distal end of the obturator extends beyond the distal end of the needle, and (ii) when the trigger carriage is in its proximal position, the distal end of the obturator is received within the distal end of the needle;
a spring for urging the trigger carriage into its distal position;
a trigger mounted to the trigger carriage for urging the trigger carriage towards its proximal position;
a first latch for releasably locking the trigger carriage in its distal position;
a second latch for releasably locking the trigger carriage in an intermediate position located between the distal position and the proximal position, wherein the distal end of the obturator partially emerges from the hollow needle;
the first latch, second latch and trigger being configured so that when the trigger carriage is in its distal position and the first latch set, and the trigger is thereafter pulled proximally, the first latch is released and the trigger carriage moves proximally into its proximal position, and thereafter releasing the trigger causes the trigger carriage to move into its intermediate position and set the second latch;

and further wherein, when the trigger carriage is in its intermediate position and the distal end of the obturator engages tissue, the trigger carriage is moved proximally so as to release the second latch;

configuring the safety needle so that the trigger carriage is in its distal position and the first latch set;

moving the trigger so that the first latch is released and the trigger carriage moves proximally into its proximal position;

releasing the trigger so as to cause the trigger carriage to move into its intermediate position and set the second latch; and advancing the safety needle so that the distal end of the needle and the distal end of the obturator engage tissue.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

Figure 1A:
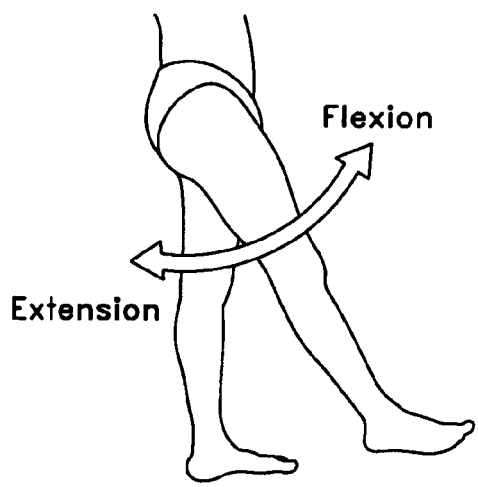
FIGS. 1A-1D are schematic views showing various aspects of hip motion.
Figure 1B:
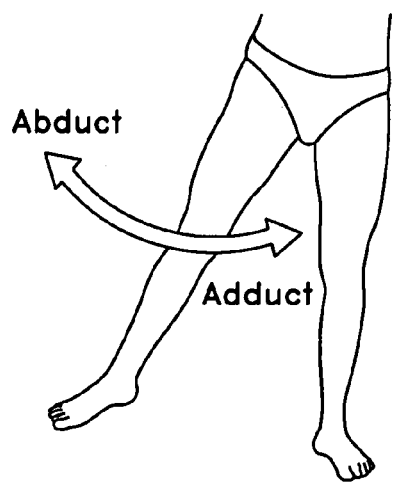
Figure 1C:
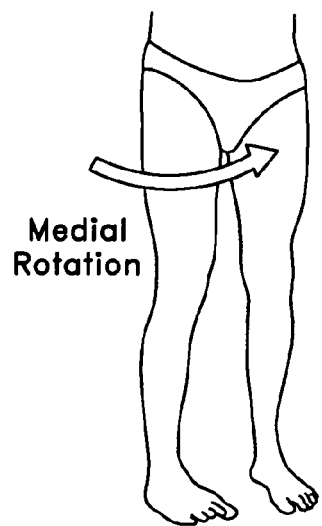
Figure 1D:
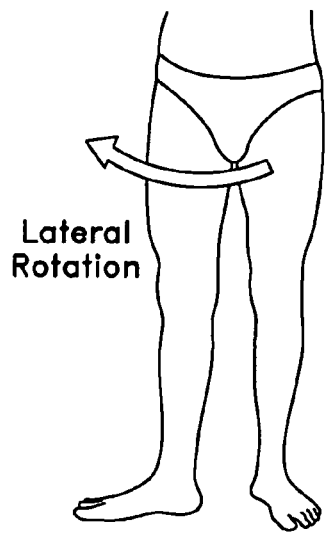
Figure 2:
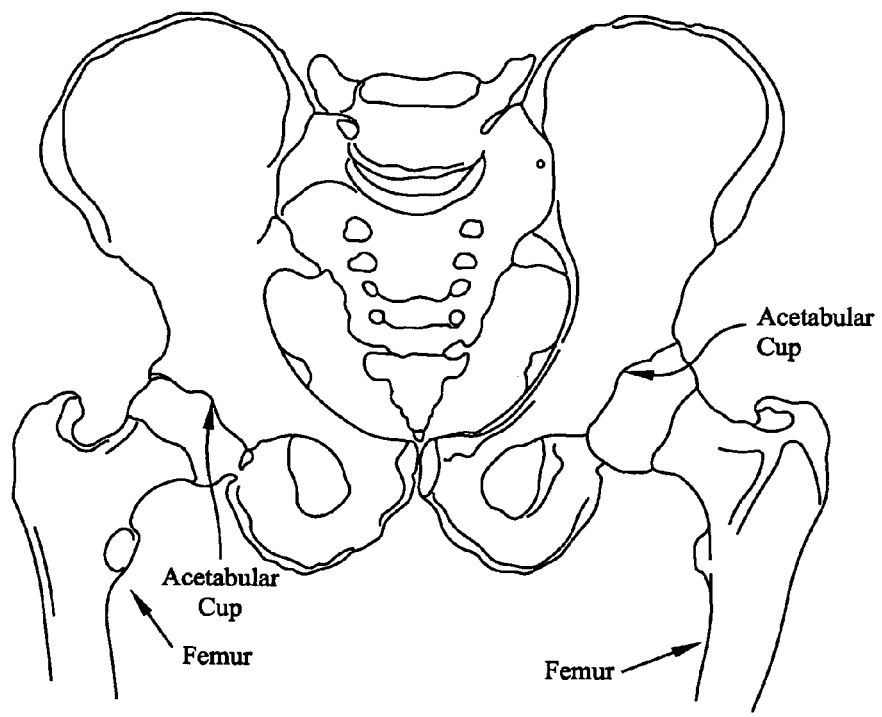
FIG. 2 is a schematic view showing the bone structure in the region of the hip joints.
Figure 3:
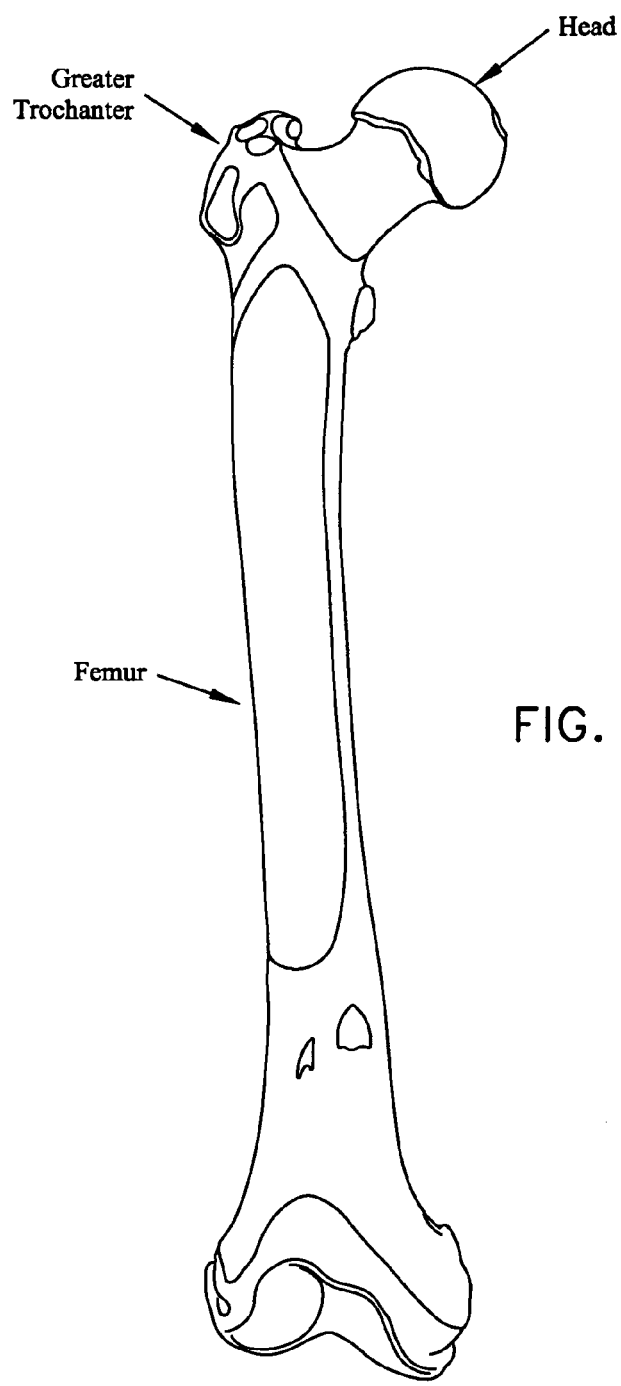
FIG. 3 is a schematic view of the femur.
Figure 4:
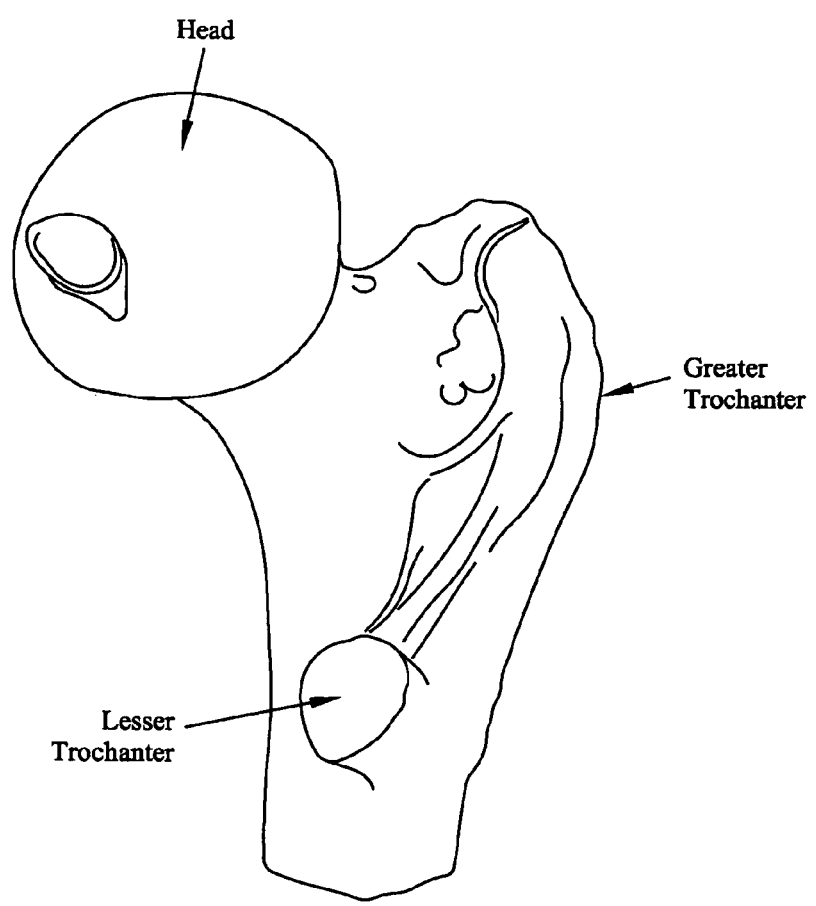
FIG. 4 is a schematic view of the top end of the femur.
Figure 5:
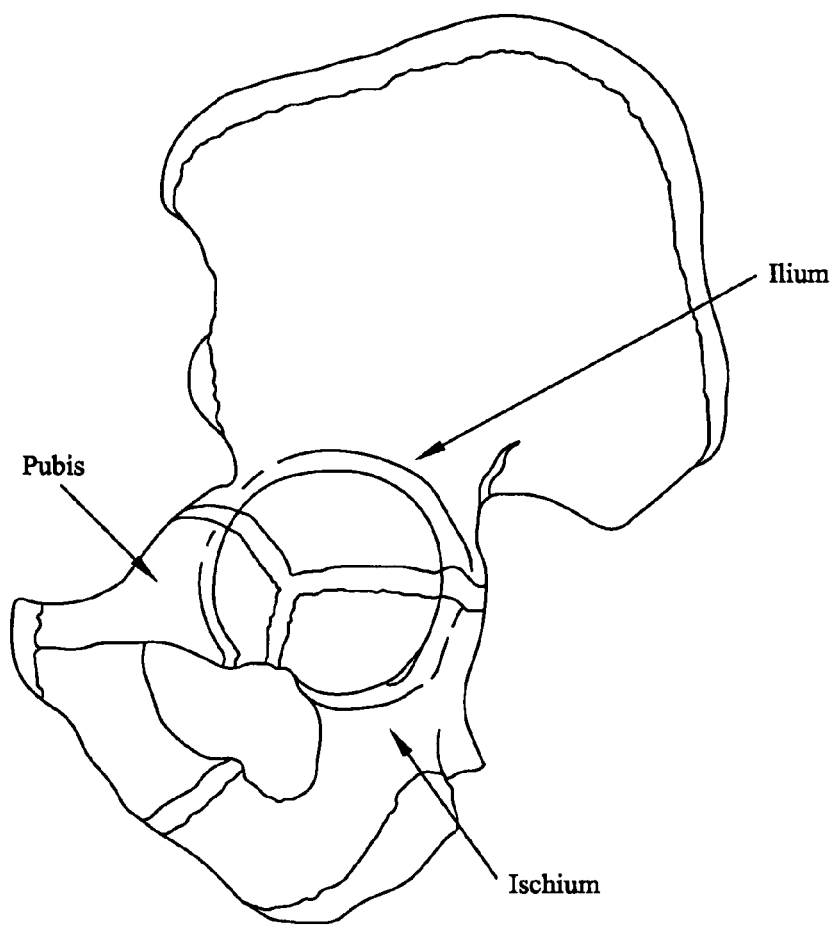
FIG. 5 is a schematic view of the pelvis.
Figure 6:
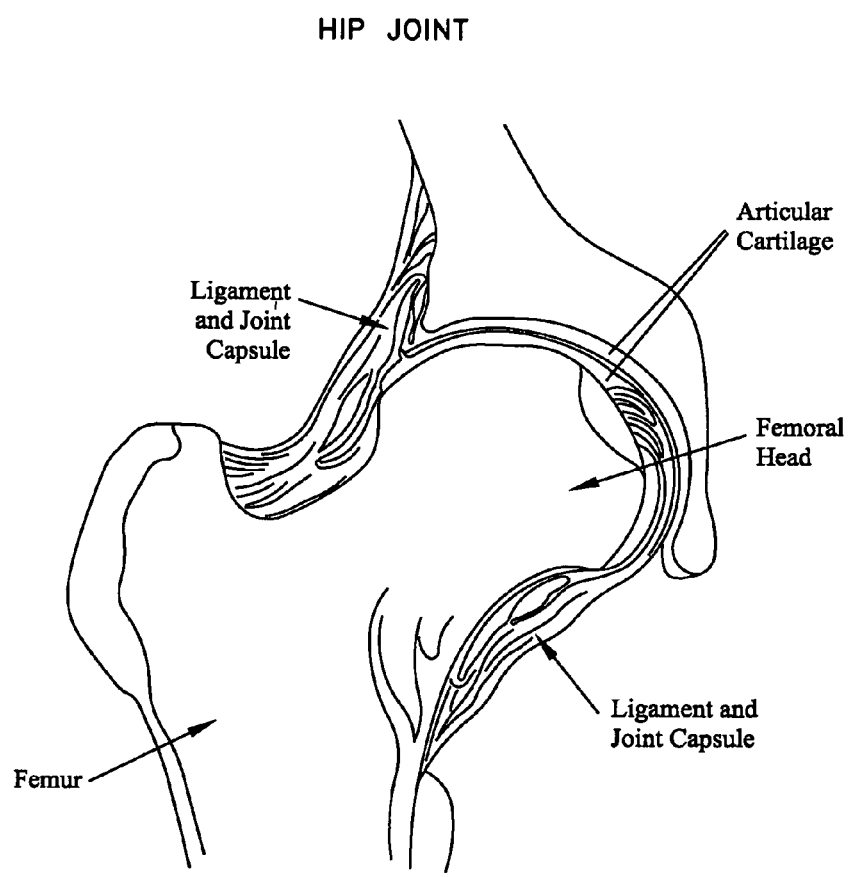
FIGS. 6-12 are schematic views showing the bone and soft tissue structure of the hip joint.
Figure 7:
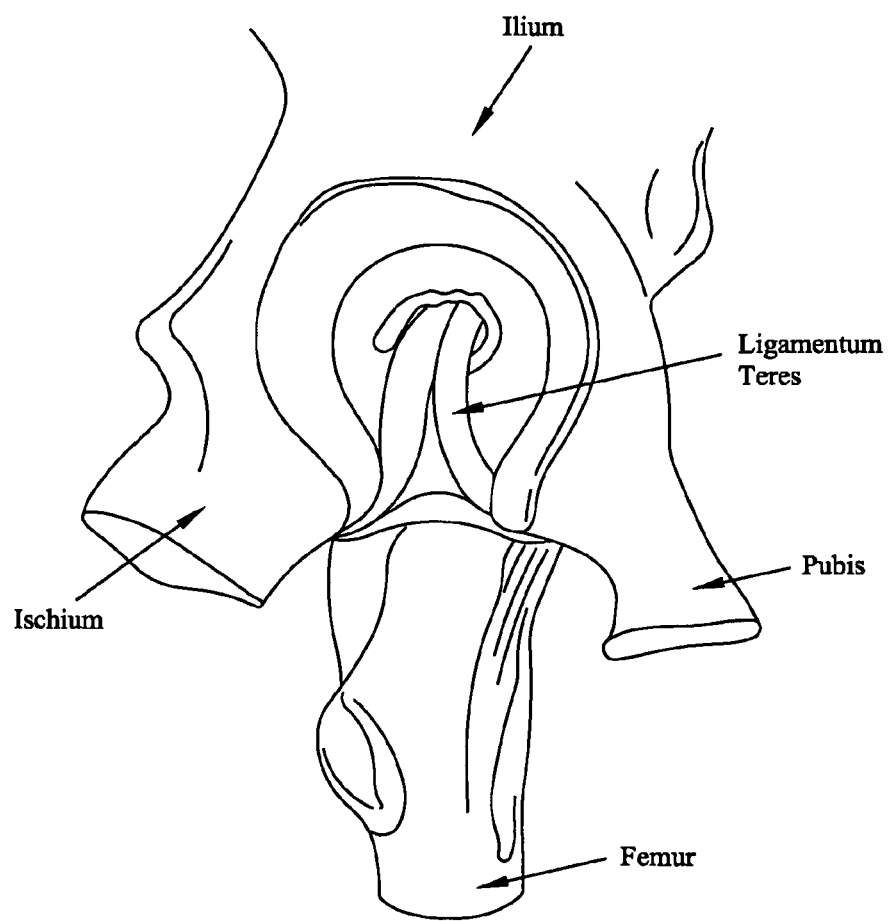
Figure 8:
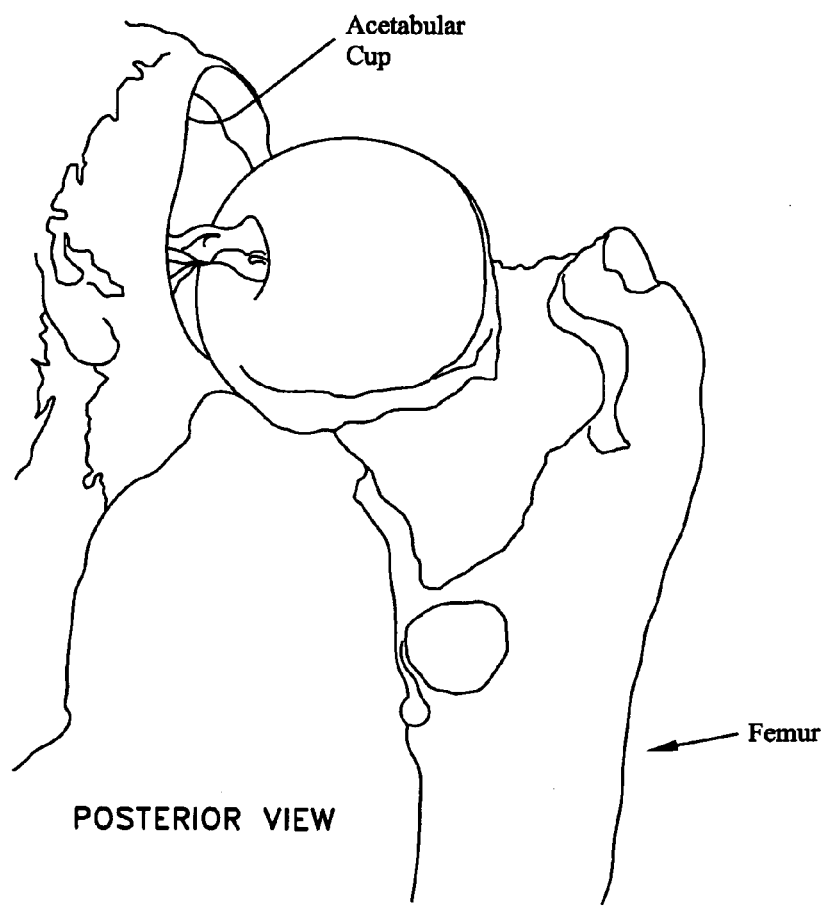
Figure 9:
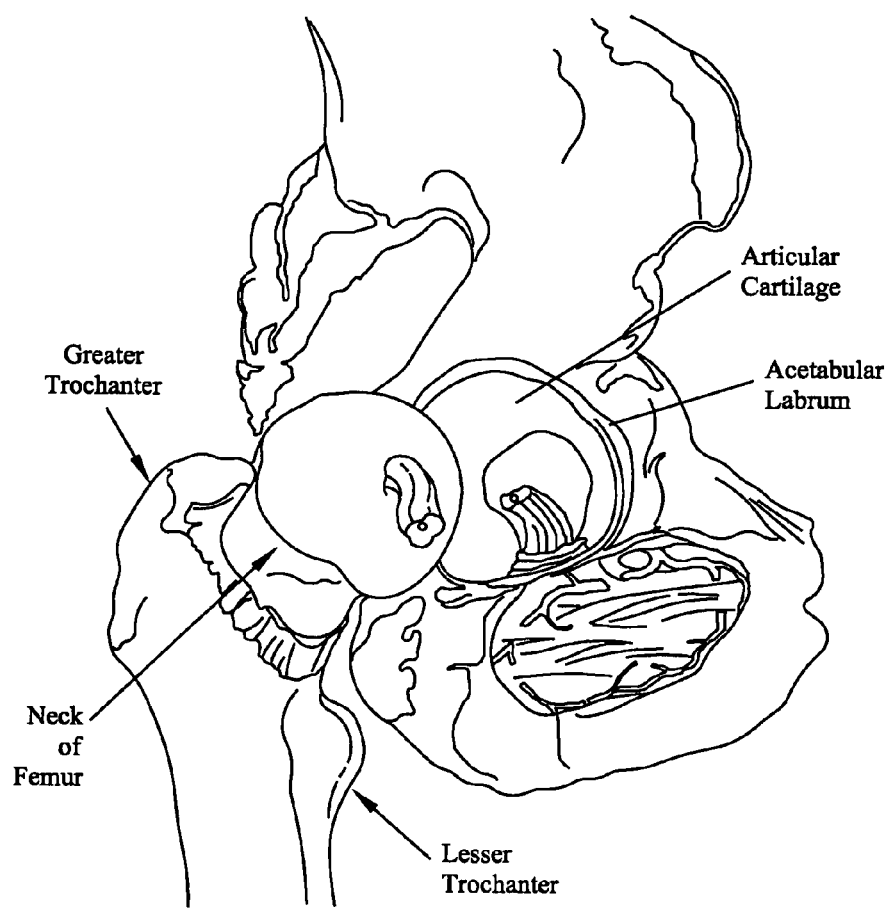
Figure 10:
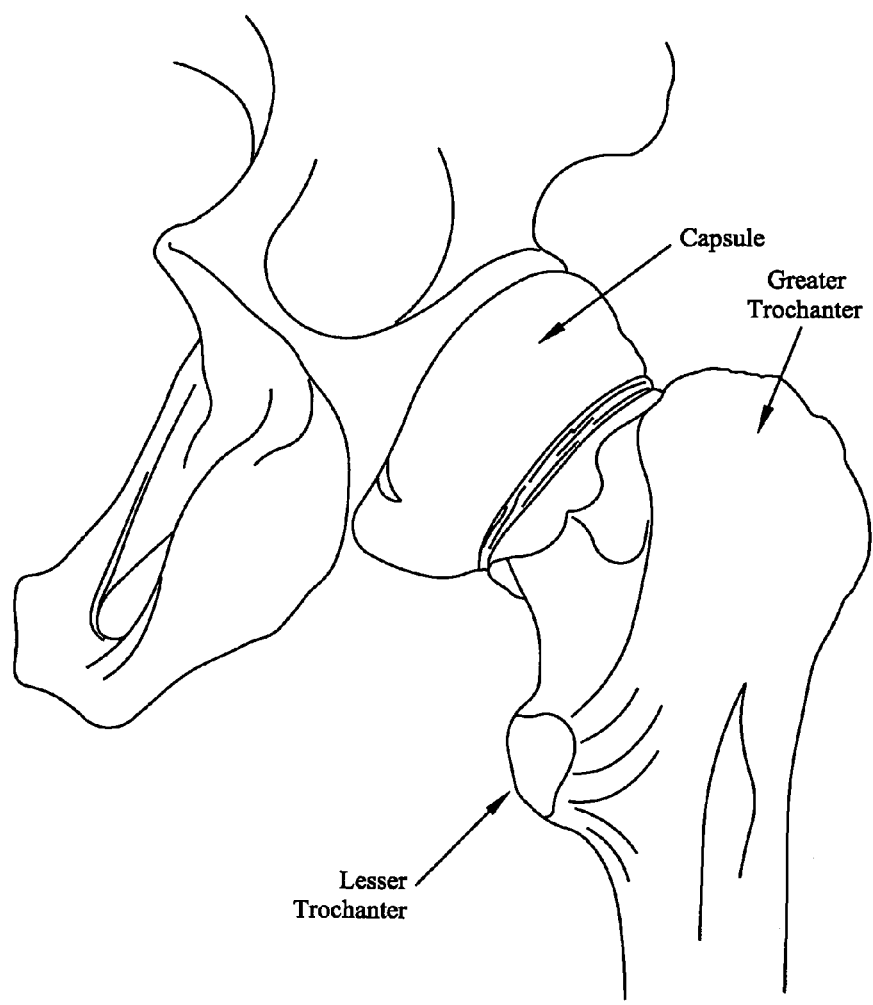
Figure 11:
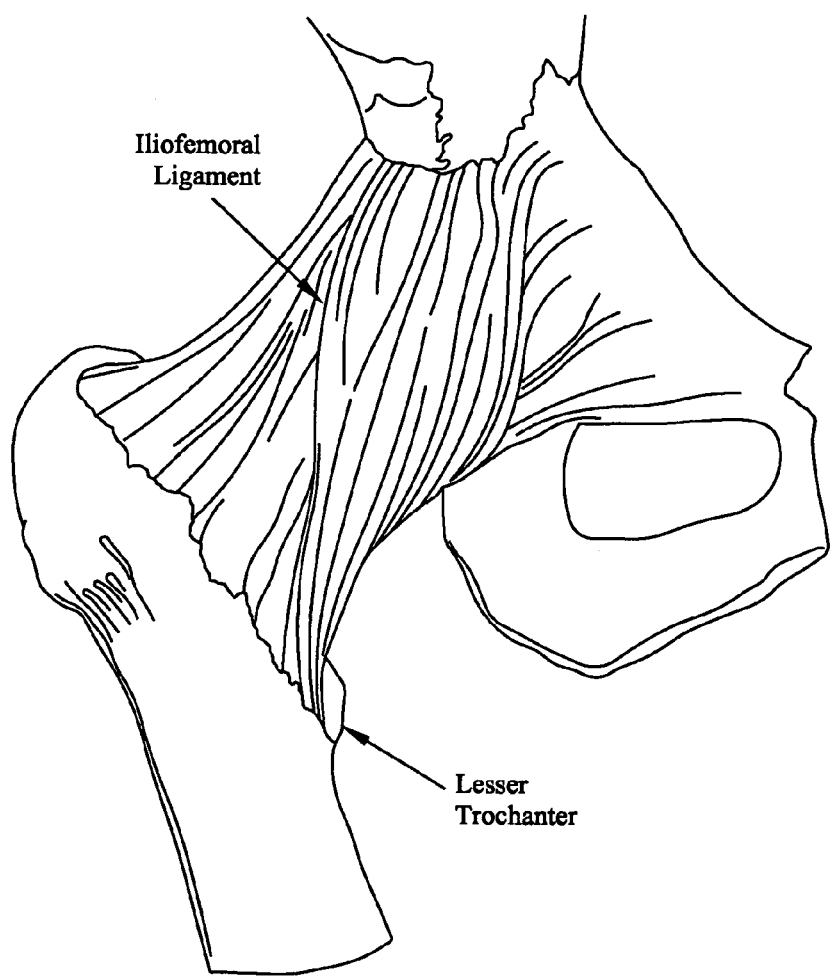
Figure 12:
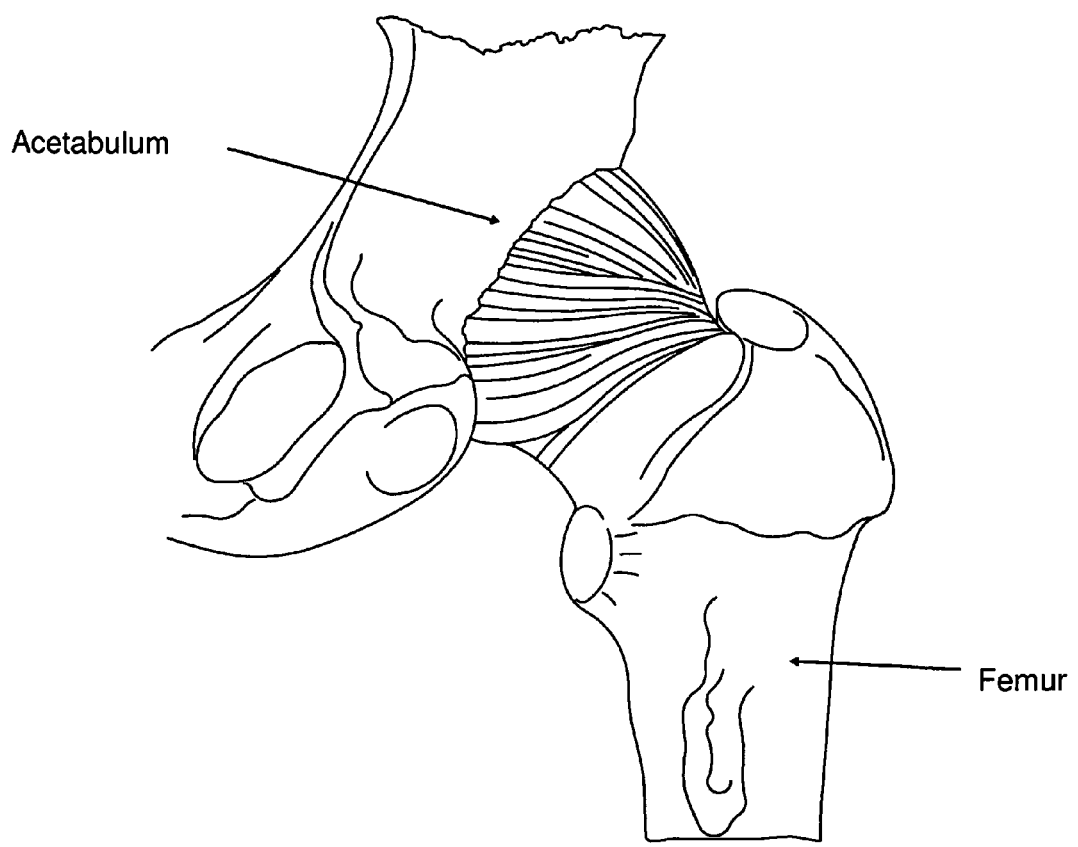
Figure 13:
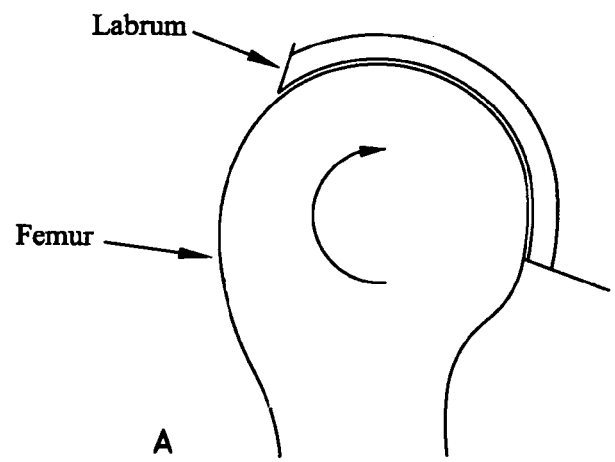
FIG. 13 is a schematic view showing cam-type femoroacetabular impingement (FAI)
Figure 13:
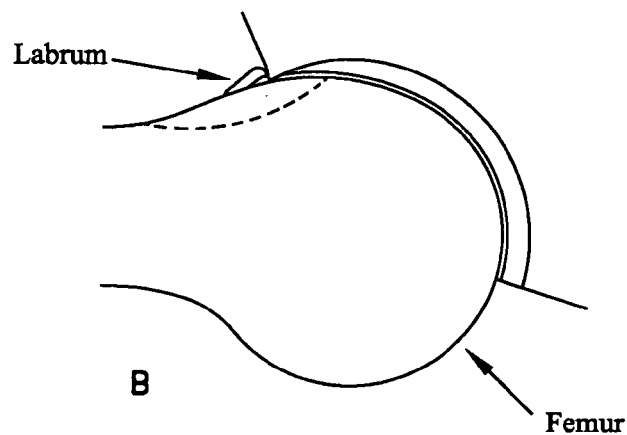
Figure 14:
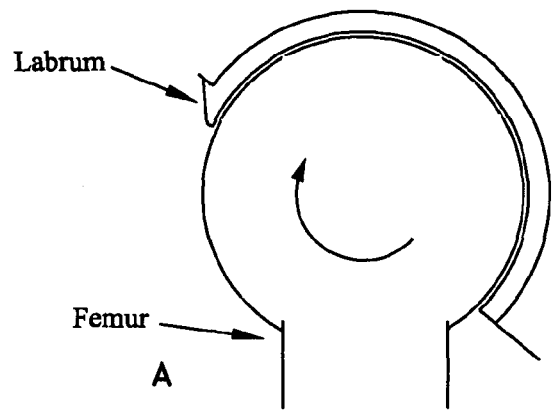
FIG. 14 is a schematic view showing pincer-type femoroacetabular impingement (FAI)
Figure 14:
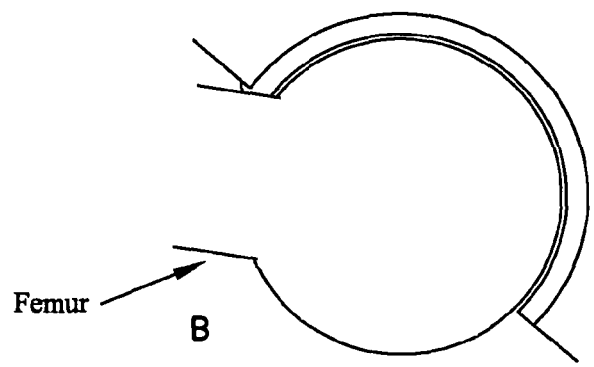
Figure 15:
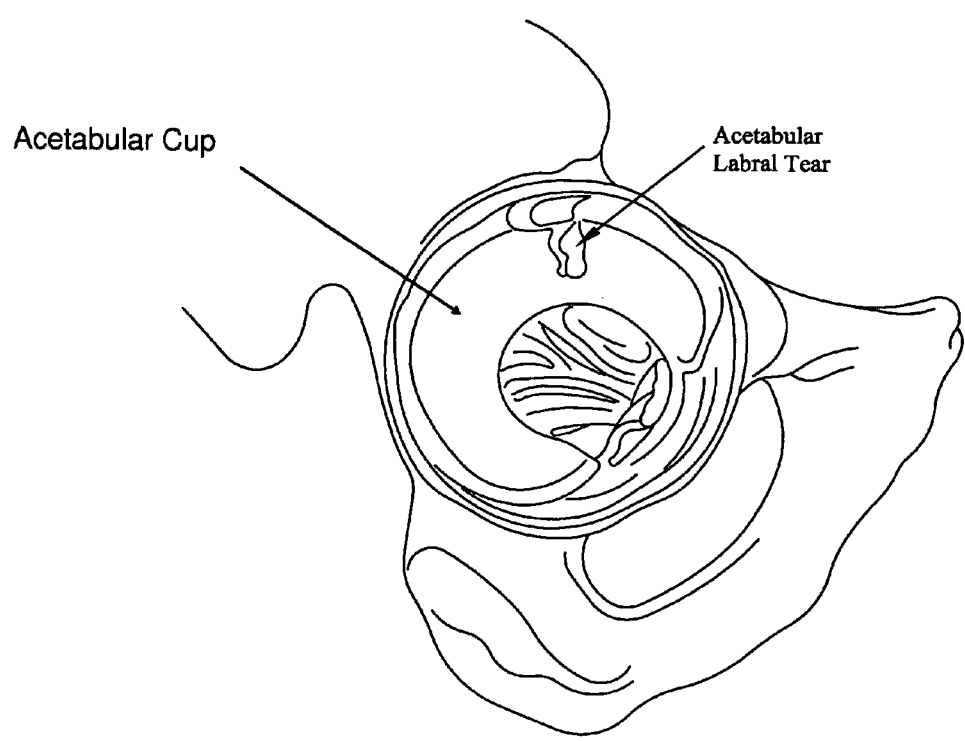
FIG. 15 is a schematic view showing a labral tear.
Figure 16:
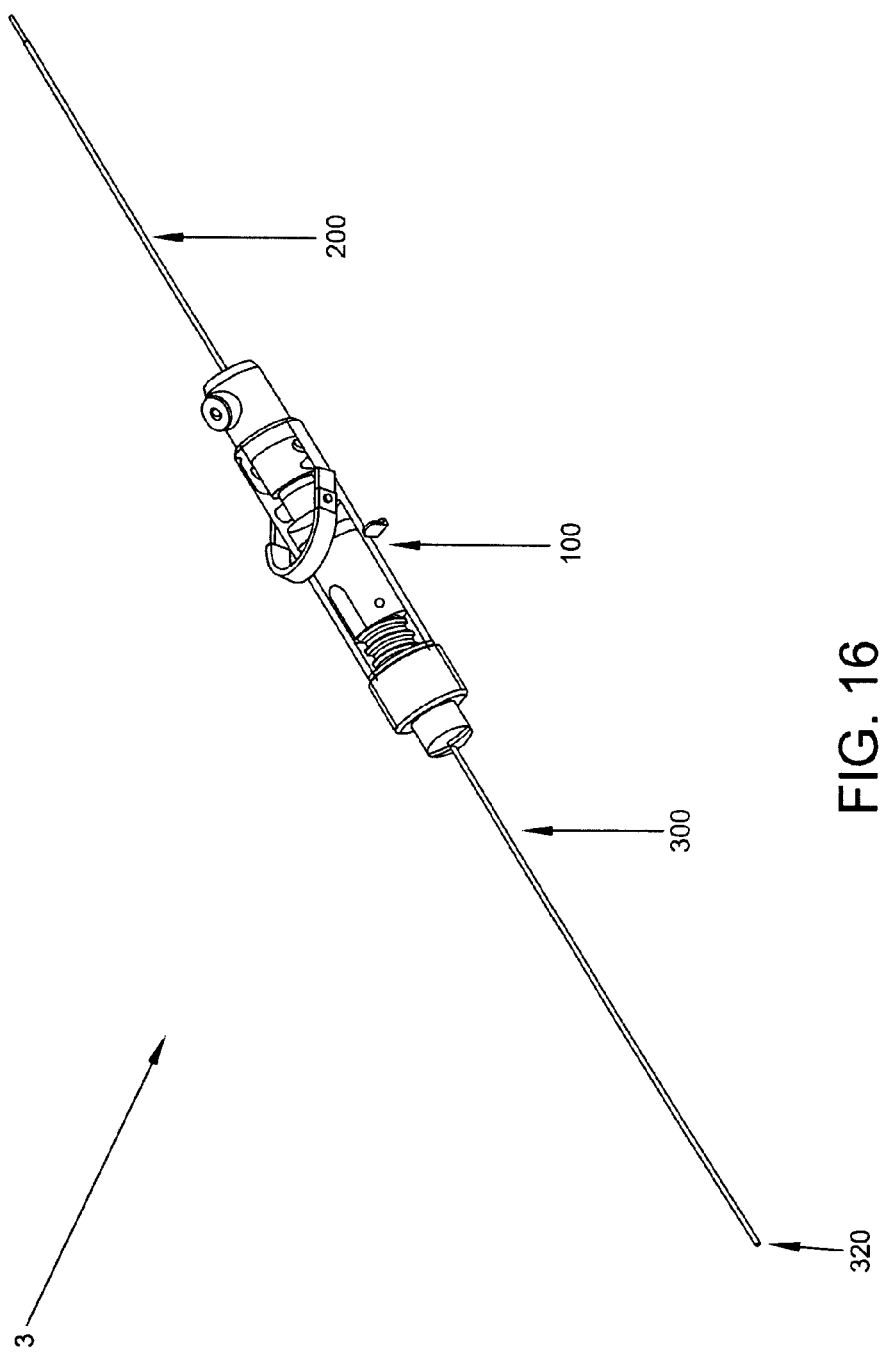
FIG. 16 is a schematic view showing a novel safety needle formed in accordance with the present invention.

Looking next at FIG. 16, there is shown a safety needle 3 formed in accordance with the present invention. Safety needle 3 generally comprises a handle assembly 100, a needle assembly 200 and an obturator 300. In general, and as will hereinafter be discussed in further detail, during use, needle assembly 200 is mounted to handle assembly 100, and obturator 300 extends through handle assembly 100 and needle assembly 200, in substantially the manner shown in FIG. 16.

Figure 17:
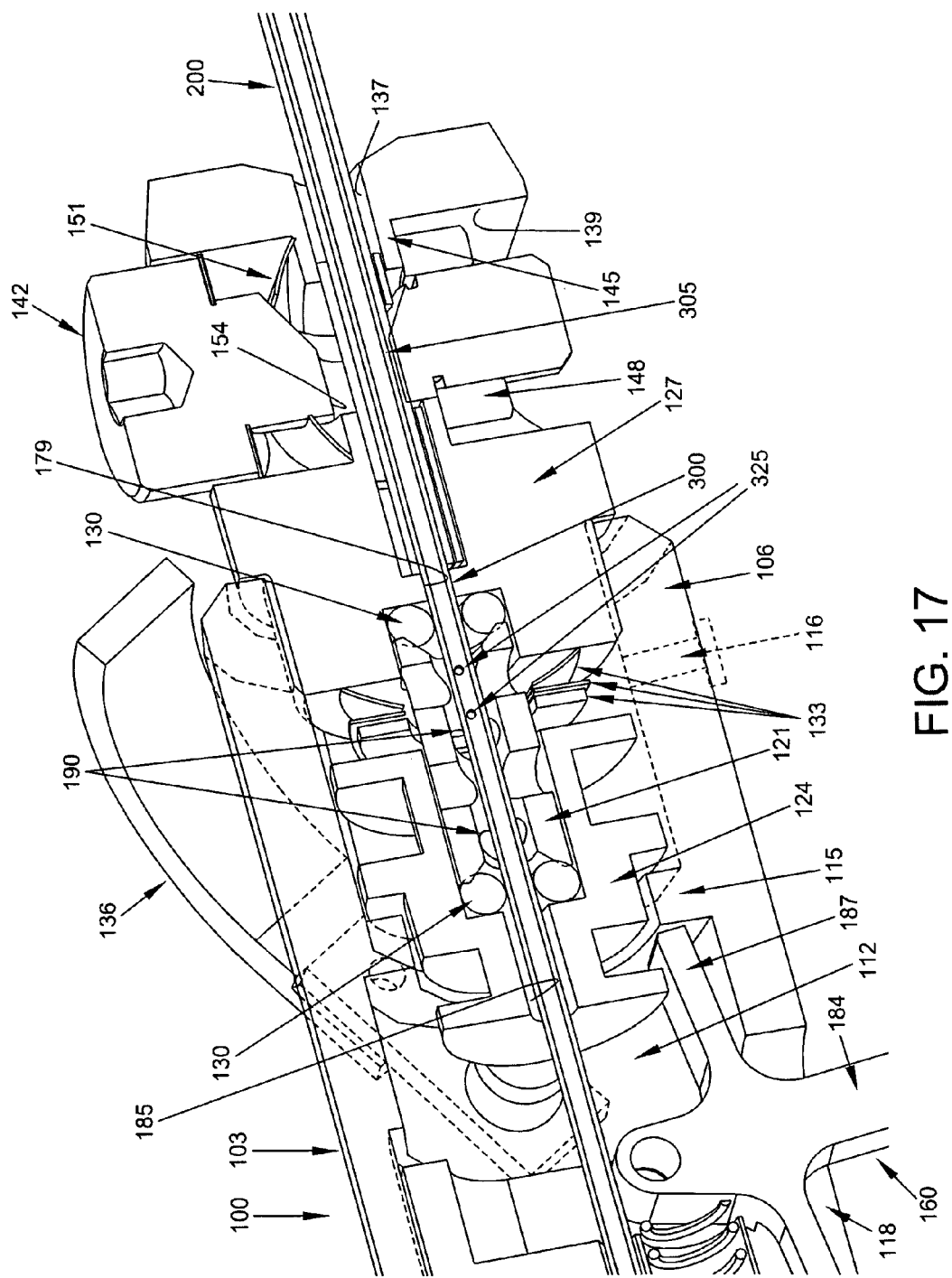
FIGS. 17 and 18 are schematic views showing various aspects of the safety needle shown in FIG. 16.
Figure 18:
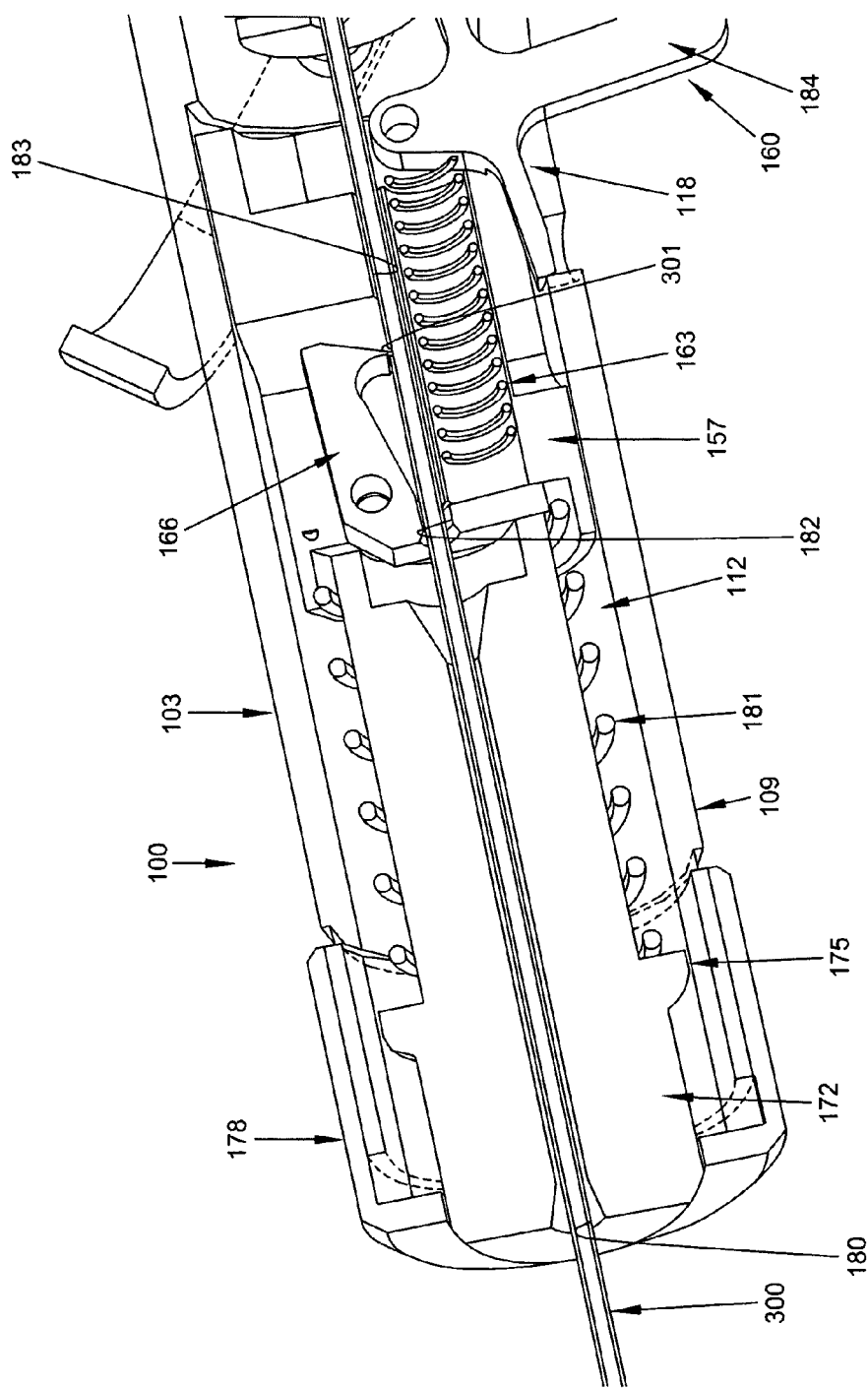

More particularly, and looking now at FIGS. 17 and 18, handle assembly 100 generally comprises a tubular housing 103 having a distal end 106, a proximal end 109 and a central lumen 112 extending therebetween. An annular wall 115 is formed intermediate the length of tubular housing 103. A side port 116 (FIG. 17) extends through the side wall of tubular housing 103, proximal to distal end 106 and distal to annular wall 115. A trigger opening 118 extends through the side wall of tubular housing 103, distal to proximal end 109 and proximal to annular wall 115.

A fluid conduit 121 is captured within tubular housing 103 between a mount 124 and a front cap 127. O-rings 130 are disposed on either end of fluid conduit 121 so as to form (i) a watertight seal between fluid conduit 121 and mount 124 and (ii) a watertight seal between fluid conduit 121 and front cap 127. Leaf springs 133 bias mount 124 against annular wall 115. A thumb lever 136 permits mount 124 to be urged distally toward front cap 127, thereby shortening the chamber holding fluid conduit 121 and O-rings 130, whereby to radially expand O-rings 130 and thereby cause the O-rings to seal against obturator 300. As a result, when thumb lever 136 urges mount 124 toward front cap 127, obturator 300 will be secured to handle assembly 100. Conversely, thumb lever 136 may be released, so that leaf springs 133 urge mount 124 proximally against annular wall 115, whereby to ease the compression of O-rings 130 and thereby release the aforementioned seal on obturator 300. As a result, when thumb lever 136 is released, obturator 300 is no longer secured to handle assembly 100 and may be removed from the handle assembly.

Front cap 127 comprises a longitudinal bore 137 for receiving needle assembly 200, and a transverse bore 139 for receiving a locking pin 142. More particularly, transverse bore 139 includes an annular flange 145, and locking pin 142 includes a locking nut 148, whereby leaf spring 151 can yieldably bias locking nut 148 against annular flange 145. A longitudinal bore 154 extends through locking pin 142 so that when the head of locking pin 142 is pressed inwardly, against the bias of leaf spring 151, longitudinal bore 154 of locking pin 142 can be aligned with longitudinal bore 137 of front cap 127; conversely, when the inward force on the head of locking pin 142 is released, leaf spring 151 causes the locking pin's longitudinal bore 154 to move out of alignment with the front cap's longitudinal bore 137. In this way, locking pin 142 can be used to selectively capture needle assembly 200 to handle assembly 100.

A trigger carriage 157 (FIG. 18) is slidably disposed within tubular housing 103, between annular wall 115 (FIG. 17) and proximal end 109 (FIG. 18). A trigger 160 is pivotally mounted to trigger carriage 157, with a spring 163 biasing trigger 160 in a distal direction. A finger 166 (FIG. 18) is pivotally mounted to trigger carriage 157, so as to selectively engage a notch 301 formed in obturator 300. A release button 172 (FIG. 18), having a peripheral flange 175, is captured between trigger carriage 157 and an end cap 178. More particularly, a spring 181 biases trigger carriage 157 and peripheral flange 175 away from one another.

Assembly

Safety needle 3 may be assembled as follows.

First, trigger 160 is pinned to trigger carriage 157, with trigger spring 163 in place, and then the components are inserted into tubular housing 103 until the trigger's finger 184 (FIG. 18) extends out the bottom of trigger opening 118.

Next, spring 181 and release button 172 are introduced into the back of tubular housing 103, and then end cap 178 is screwed into place.

Then mount 124 (FIG. 17), fluid conduit 121 and O-rings 130 are inserted into the distal end of tubular housing 103, and thereafter secured in place using front cap 127.

Next, locking pin 142 is pressed inwardly so that its longitudinal bore 154 is moved into alignment with the front cap's longitudinal bore 137. Then needle assembly 200 is inserted into longitudinal bore 137 of front cap 127 and through longitudinal bore 154 of locking pin 142. Then locking pin 142 is released, thereby locking needle assembly 200 to handle assembly 100, with the interior of needle assembly 200 communicating with the interior of tubular housing 103 via an opening 179 formed in the proximal end of cap 127.

Finally, obturator 300 is advanced through (i) an opening 180 formed in release button 172, (ii) an opening 182 formed in the proximal end of finger 166, (iii) an opening 183 formed in trigger carriage 157, (iv) the interior of tubular housing 103, (v) an opening 185 formed in mount 124, (vi) the proximal O-ring 130, (vii) the interior of fluid conduit 121, (viii) the distal O-ring 130, (ix) opening 179 formed in the proximal end of front cap 127, and (x) needle assembly 200, until notch 301 (FIG. 18) is engaged by finger 166, whereby to releasably secure obturator 300 to handle assembly 100.

Figure 19:
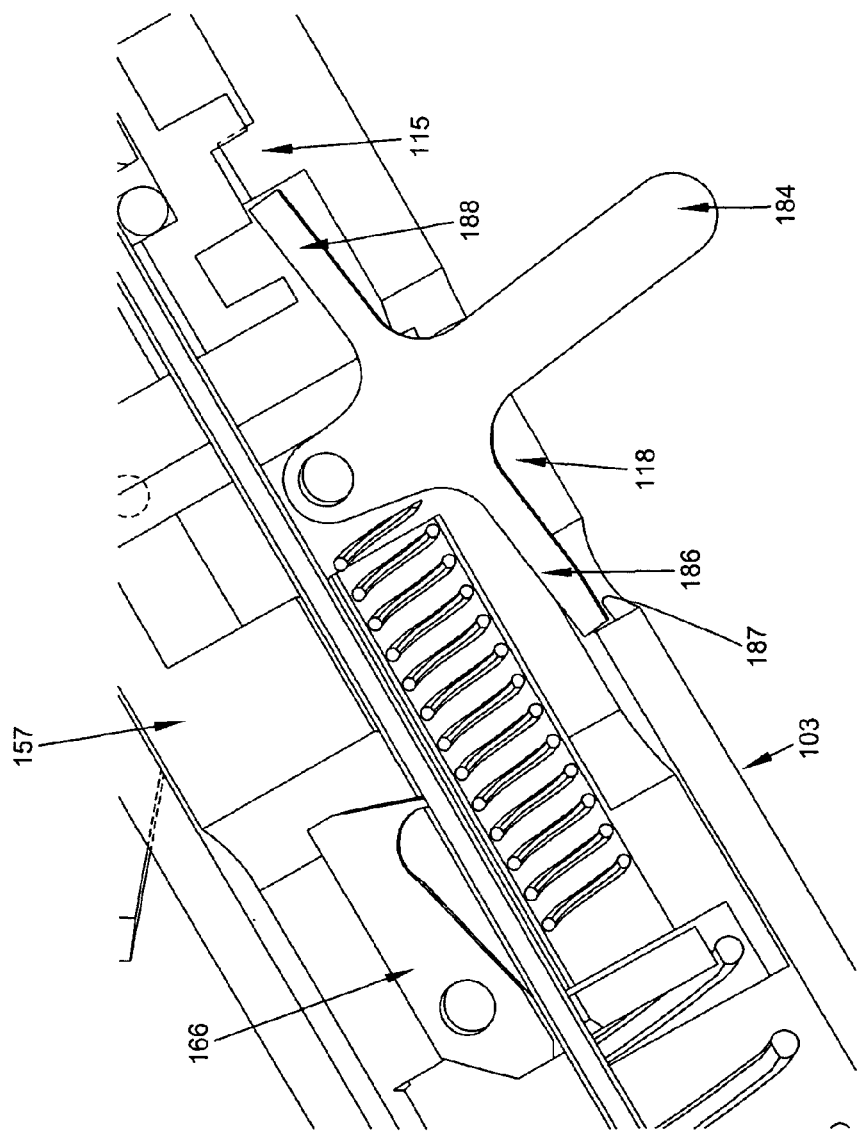
FIGS. 19 and 20 are schematic views showing the safety needle of FIG. 16 after assembly and prior to use.
Figure 20:
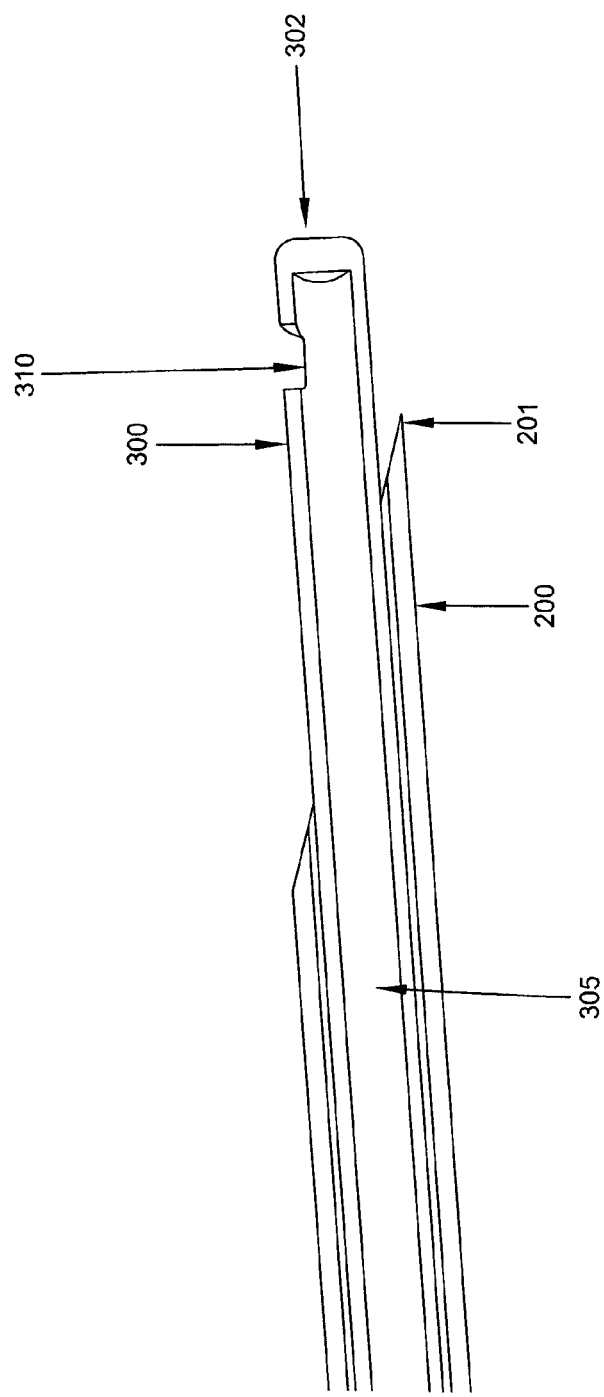

At this point, safety needle 3 is disposed in the condition shown in FIGS. 19 and 20. More particularly, the trigger's proximal arm 186 is in engagement with the proximal end 187 of trigger opening 118 (FIG. 19), and obturator 300 is in its extended position (FIG. 20), whereupon the sharp distal tip 201 of needle assembly 200 is proximal to, and shielded by, the projecting distal tip 302 of the extended obturator 300.

The safety needle may now be sterilized and packaged for shipping.

Operation

During use, safety needle 3 is first removed from its sterile package.

Then end cap 178 (FIG. 18) is screwed towards or away from tubular housing 103 so as to set the appropriate tension on trigger carriage 157 via spring 181.

Figure 21:
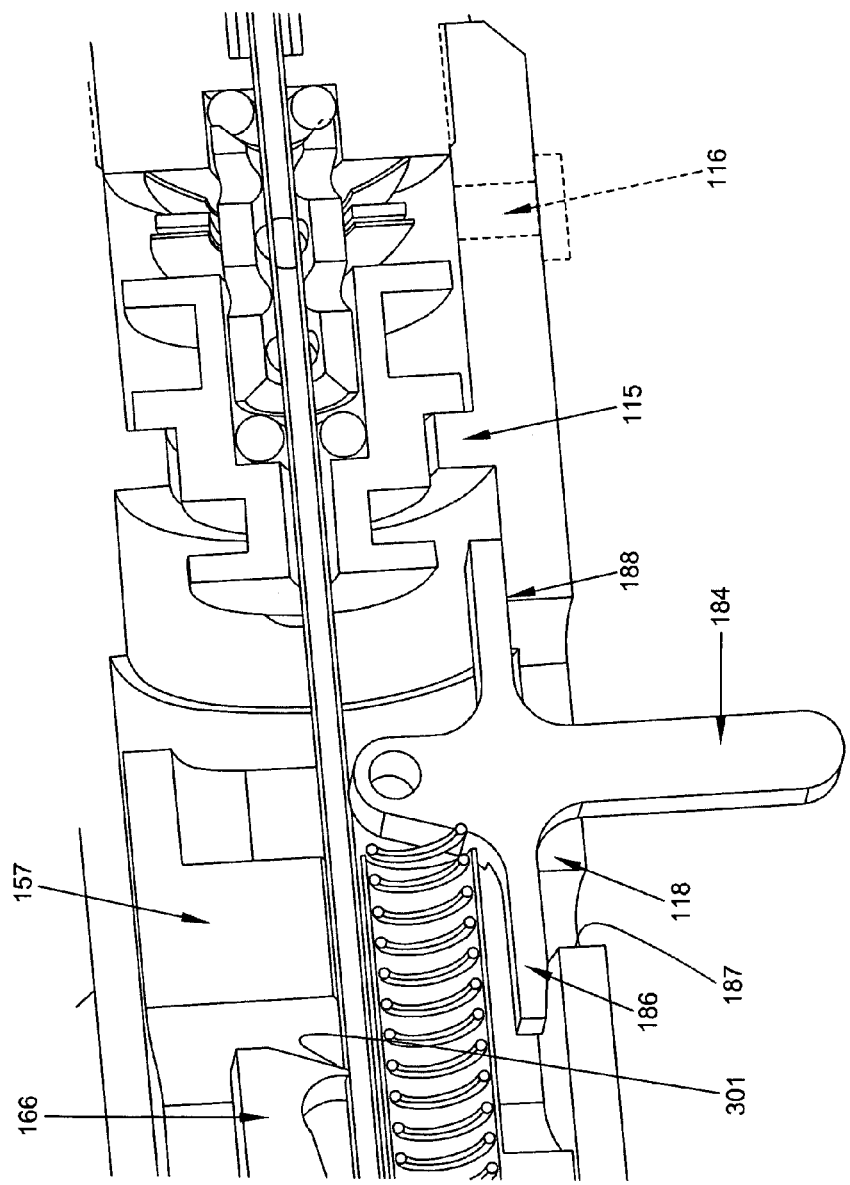
FIGS. 21-24 are schematic views showing the safety needle of FIG. 16 being placed into its "cocked" condition, with the trigger being pulled a first step so as to put the safety needle in a first, partially-cocked condition (FIGS. 21 and 22) and with the trigger thereafter being pulled a second step so as to put the safety needle into a second, fully-cocked condition (FIGS. 23 and 24)
Figure 22:
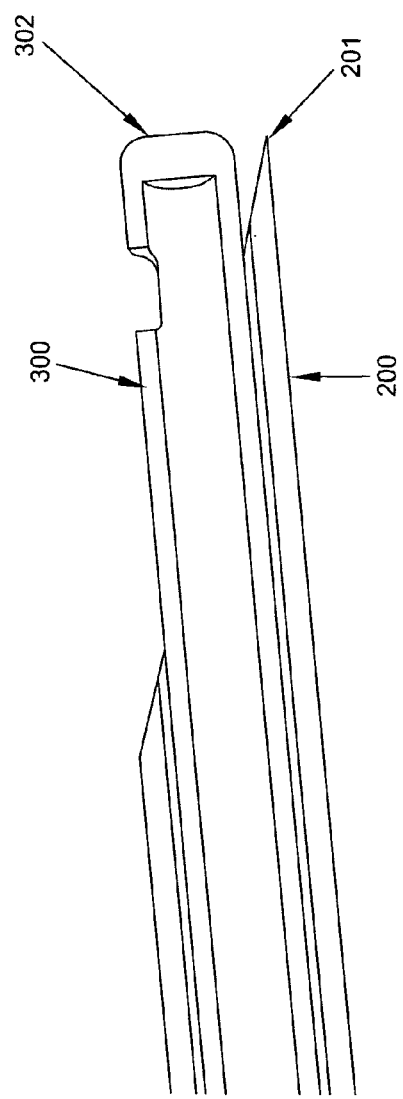
Figure 23:
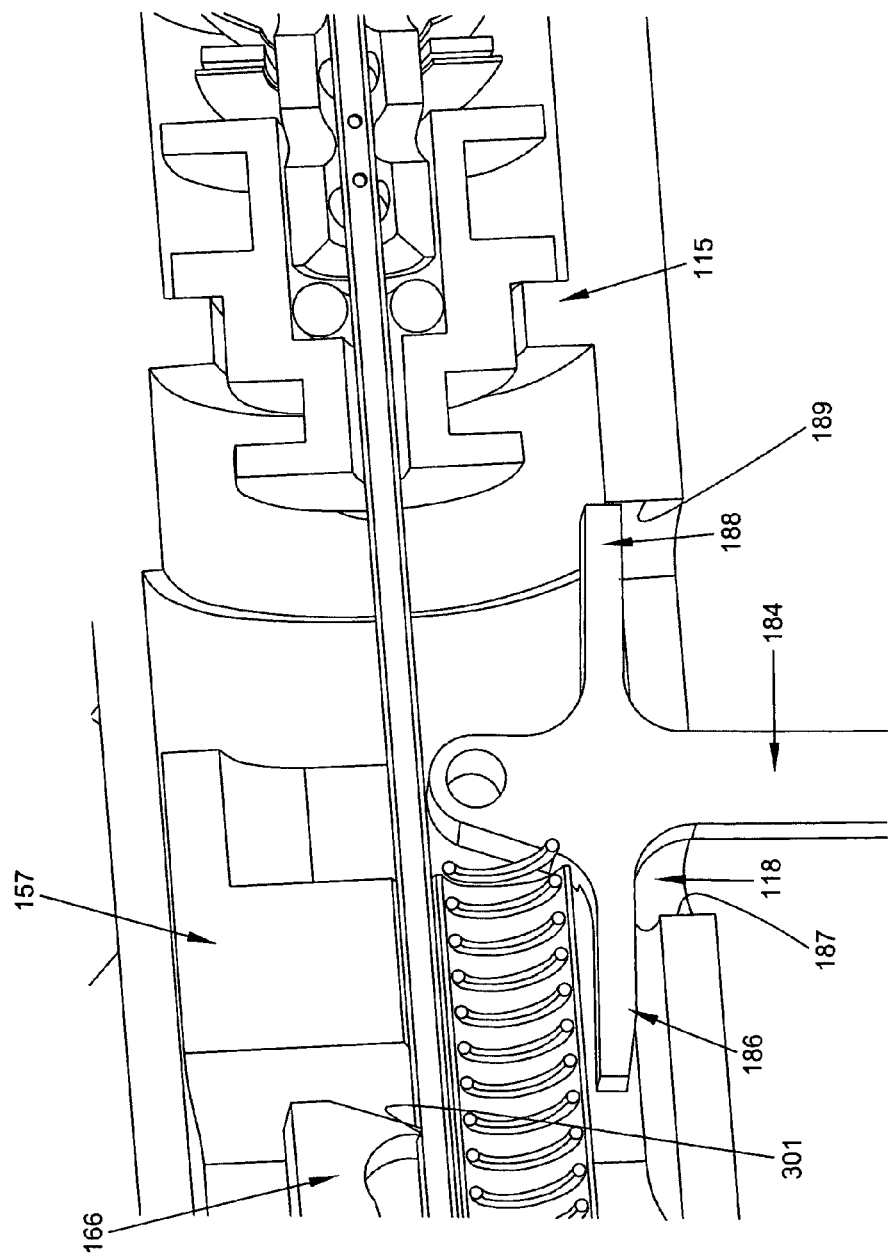
Figure 24:
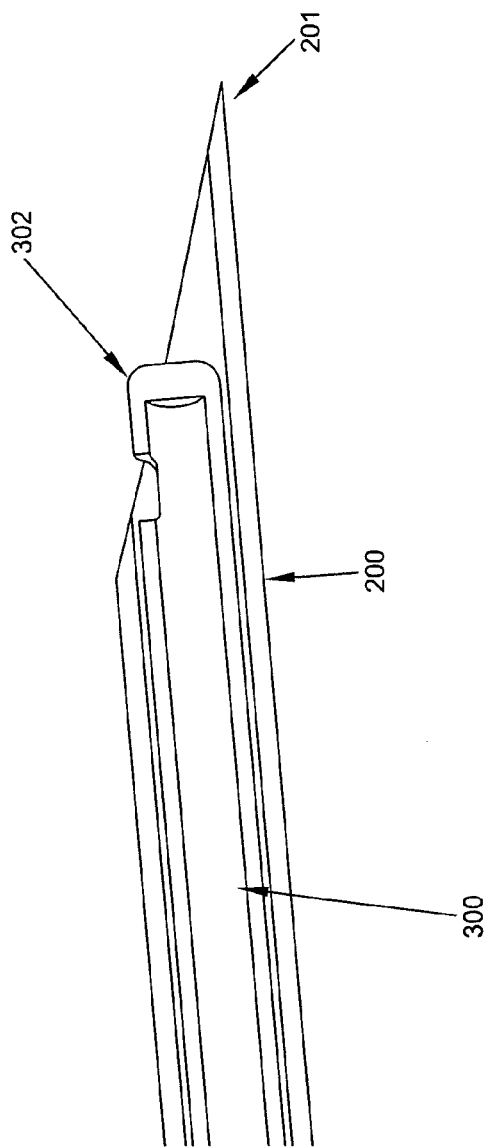

Next, safety needle 3 is "cocked" by pulling trigger finger 184 proximally, so as to rotate the complete trigger 160 in a clockwise direction. As this occurs, trigger finger 184 is first disposed intermediate trigger opening 118, with the trigger's proximal arm 186 and distal arm 188 substantially parallel to obturator 300, and with distal tip 302 of obturator 300 approximately aligned with distal tip 201 of needle assembly 200 (see FIGS. 21 and 22). Trigger finger 184 is pulled further back until the safety needle is placed into its "cocked" position (FIGS. 23 and 24), with distal arm 188 of trigger finger 184 engaging the distal end 189 of trigger opening 118, and with distal tip 302 of obturator 300 residing just proximal to, yet protruding slightly out of, distal tip 201 of needle assembly 200.

Figure 25:
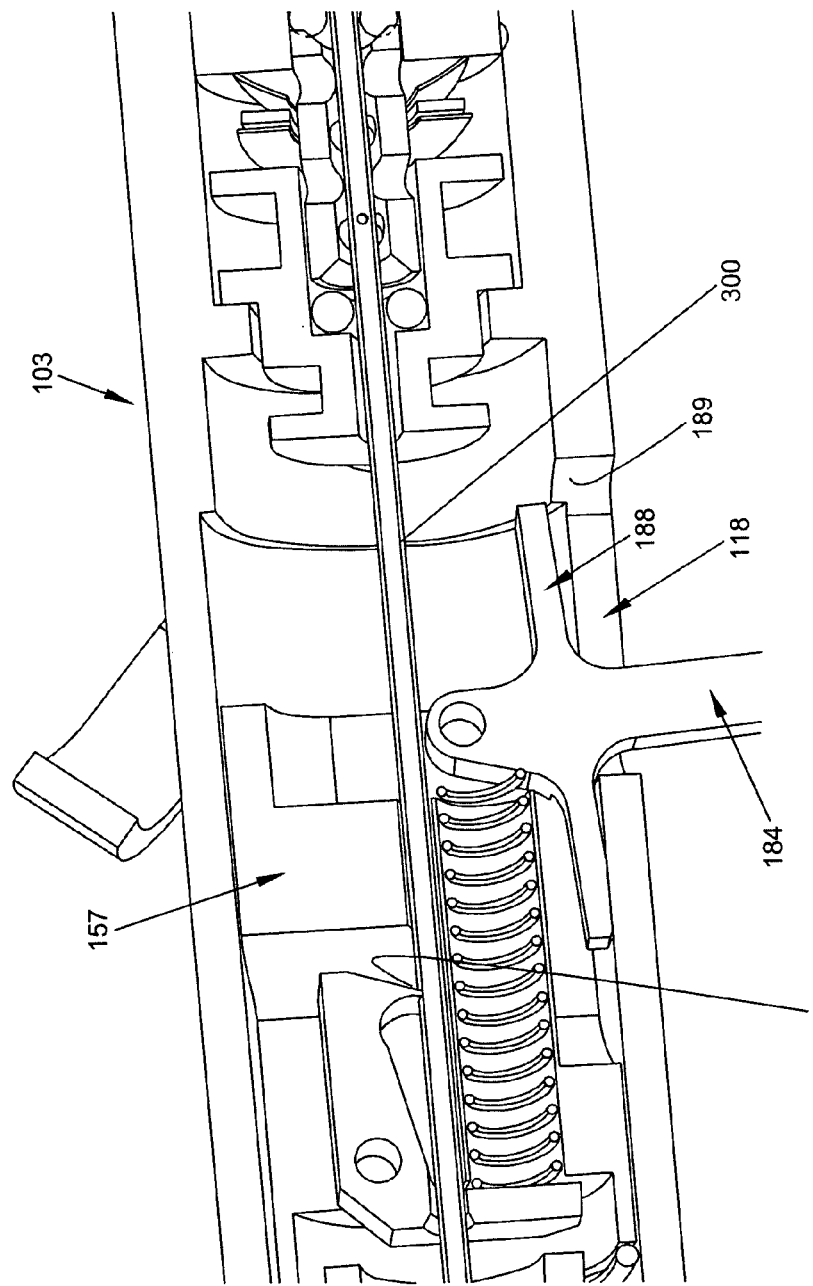
FIGS. 25 and 26 are schematic views showing the condition of the safety needle as it is advanced through tissue.
Figure 26:
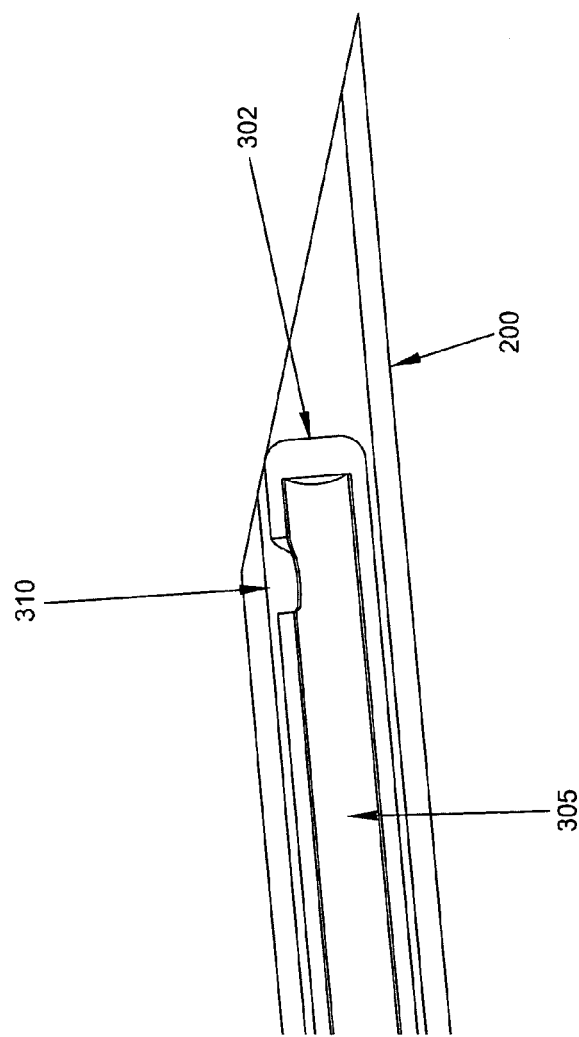

With safety needle 300 in this condition, the safety needle is advanced into the patient. As the safety needle is forced through the tissue of the patient, obturator 300 is urged proximally, further into needle assembly 200, by virtue of the engagement of the distal tip of the obturator with the tissue. At the same time, trigger carriage 157 is urged proximally due to the engagement of finger 166 with notch 301 of obturator 300. This action causes the trigger's distal arm 188 to pivot counterclockwise, releasing distal arm 188 from its engagement with the distal end 189 of trigger opening 118 (see FIGS. 25 and 26).

The safety needle is held in this equilibrium condition as the safety needle is advanced through the tissue, by virtue of the proximally-directed force imposed on the advancing obturator by the intervening tissue.

Figure 27:
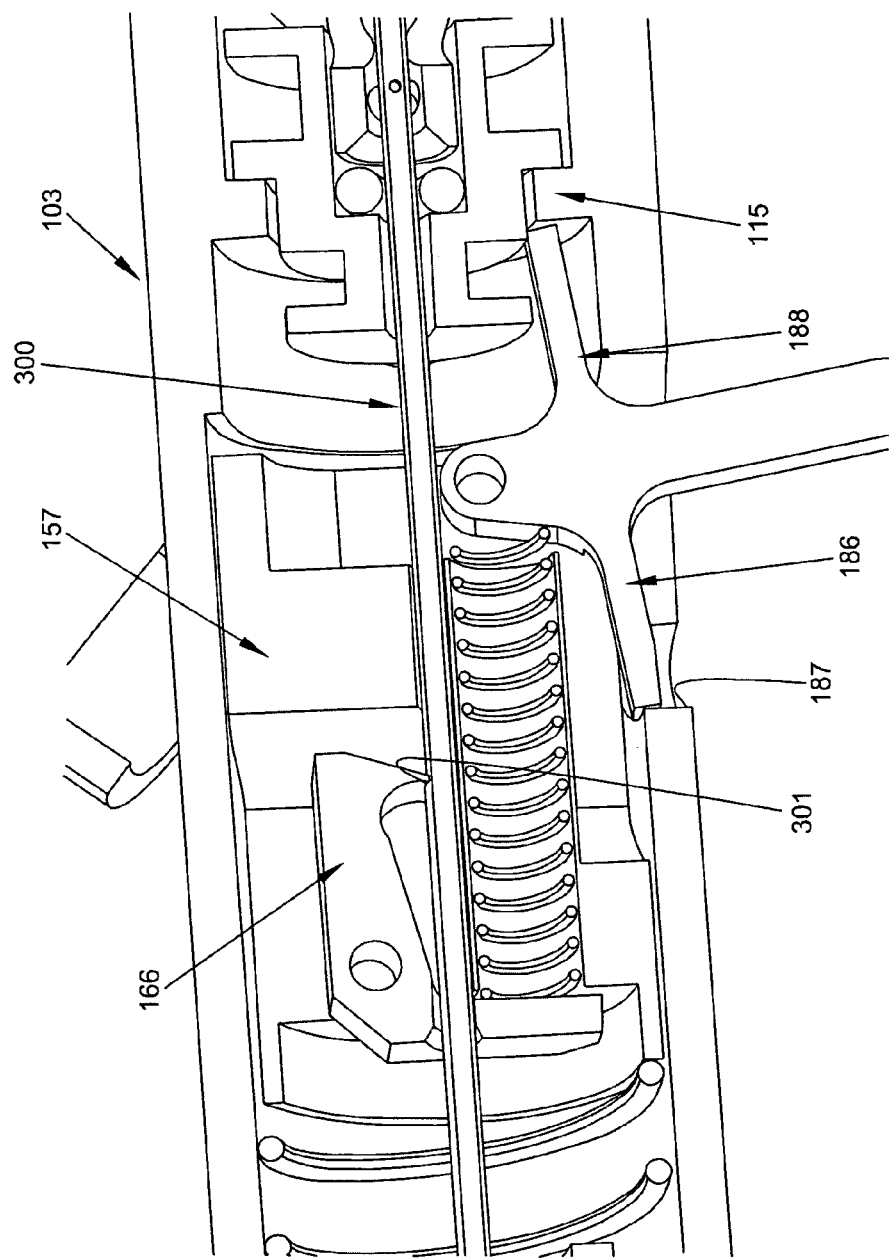
FIGS. 27 and 28 are schematic views showing the condition of the safety needle immediately after the distal end of the safety needle passes through intervening tissue and enters the interior of the joint.
Figure 28:
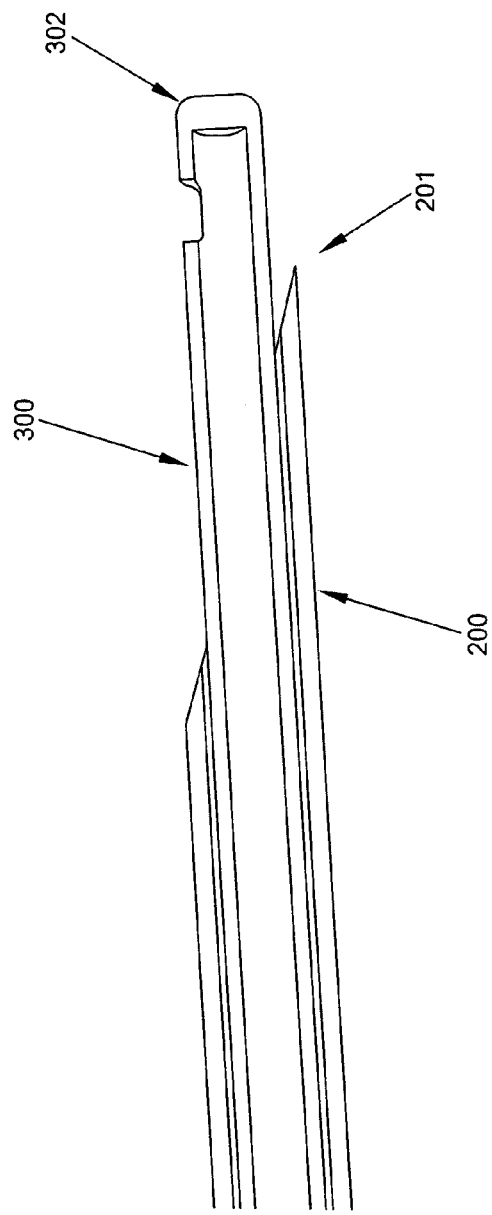

As soon as safety needle 3 penetrates through the tissue, so that there is no longer a proximally-directed force acting on distal tip 302 of obturator 300, trigger carriage 157 "pops" forward, carrying obturator 300 with it by virtue of the engagement of finger 166 with notch 301. Trigger carriage 157 and obturator 300 move forward as a unit until the trigger's distal arm 188 encounters annular wall 115, whereupon obturator 300 will project out the distal end of needle assembly 200 (FIGS. 27 and 28). As this occurs, the trigger's proximal arm 186 rotates counterclockwise to engage proximal end 187 of trigger opening 118 (FIG. 27). This action locks obturator 300 in its extended position (FIG. 28), whereupon sharp distal tip 201 of needle assembly 200 resides proximal to blunt distal tip 302 of obturator 300, and is as such prevented from engaging tissue due to the shielding tip of obturator 300.

It will be appreciated that, at this point, safety needle 3 will have returned to the "starting position" shown in FIGS. 19 and 20, i.e., the condition it was in when it was removed from the sterile packaging.

At this point, needle assembly 200 can be disassembled from handle assembly 100 (i.e., by depressing locking pin 142), and then handle assembly 100 and obturator 300 can be removed from the surgical site, thereby leaving needle assembly 200 extending from a point outside the body down to the surgical site. Tissue dilators may then deployed over needle assembly 200 so as to dilate the tissue disposed between the skin and the interior of the joint. Then an access cannula may be inserted over needle assembly 200. Thereafter, the needle assembly 200 may be withdrawn, leaving the access cannula available for passing instruments and the like down to the surgical site.

Use of the Safety Needle in Conjunction with Fluids

During hip surgery, it can be helpful to introduce fluids into the interior of the hip joint and/or to remove fluids from the interior of the hip joint. By way of example but not limitation, a saline flush can be used at the surgical site to improve visibility (e.g., to remove blood) and to flush away particles (e.g., surgical debris). Furthermore, fluids can be used to administer therapeutic agents (e.g., pharmaceuticals, growth factors, etc.) to the surgical site. In addition, fluids can be used to help "break" the suction seal which normally exists between the ball of the femur and the acetabular cup.

Safety needle 3 is constructed so as to facilitate (i) the delivery of fluids into the interior of the hip joint and/or (ii) the withdrawal of fluids from the interior of the hip joint.

More particularly, obturator 300 is preferably formed so that it has an interior lumen 305 (FIG. 17). Lumen 305 extends between (i) an opening 310 (FIG. 26) formed just proximal to distal tip 302 of obturator 300, and (ii) the proximal end 320 (FIG. 16) of obturator 300. As a result, fluid can be passed to and from the surgical site via the proximal end 320 of obturator 300. In this respect it should also be appreciated that, by forming the obturator's distal tip 302 with a "closed wall" configuration, and by positioning opening 310 in the sidewall of the obturator just proximal to distal tip 302 of the obturator, tissue coring during safety needle insertion will be prevented while still preserving fluid access to and from the surgical site.

In addition to the foregoing, and looking now at FIG. 17, obturator 300 preferably is also provided with one or more sidewall openings 325. Sidewall openings 325 communicate with openings 190 formed in the sidewall of fluid conduit 121. As a result, fluid from the interior of lumen 305 communicates (via sidewall openings 325 and openings 190) with the chamber formed between annular wall 115 and front cap 127. Side port 116 (FIG. 17), equipped with a removable closure, is formed in the sidewall of tubular housing 103 so as to permit fluid to be selectively passed to and from the surgical site via side port 116, openings 190 in fluid conduit 121, sidewall openings 325 in obturator 300 and lumen 305 in obturator 300. O-rings 130 prevent any fluid within the interior of fluid conduit 121 from escaping along the exterior of obturator 300.

Combining Obturator Function with Guidewire Function

In many situations, surgical instruments and/or implants may be introduced to, and/or removed from, the surgical site by (i) forming the surgical instruments and/or implants with a cannulated construction, and (ii) running the cannulated instruments and/or implants coaxially down a guidewire to the surgical site. By way of example but not limitation, such an approach is commonly used in many minimally-invasive surgical procedures.

In accordance with the present invention, obturator 300 can be formed and utilized so as to provide both obturator function and guidewire function.

More particularly, in one form of the present invention, after safety needle 3 has been introduced into the interior of the hip joint, handle assembly 100 and needle assembly 200 may be withdrawn (preferably as a unit) over the distal end of obturator 300, thereby leaving obturator 300 extending from a point outside of the body down to the surgical site. Cannulated surgical instruments and/or cannulated surgical implants may then be introduced to, and/or removed from, the surgical site by running those cannulated devices coaxially over obturator 300.

Thus, for the purposes of the present invention, obturator 300 may be considered to be a guidewire as well as an obturator.

Use of the Safety Needle for Other Joints, Etc

It should be appreciated that safety needle 3 may also be used for accessing joints in addition to the hip joint, e.g., safety needle 3 may be used to access the knee joint, the shoulder joint, etc. Furthermore, safety needle 3 may also be used to access other interior bodily spaces, e.g., regions around the spine, the abdominal cavity, the chest cavity, etc. In essence, safety needle 3 may be used in any circumstance where it is desired to safely advance a sharp needle into the body through intervening tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for accessing the interior of a hip joint, the method comprising:
    providing a safety needle comprising:
        a handle;
        a hollow needle fixedly mounted to the handle, the hollow needle having a sharp distal end;
        a trigger carriage slidably mounted to the handle for movement between a distal position and a proximal position;
        an obturator mounted to the trigger carriage and slidably received within the hollow needle, the obturator having a distal end wherein the distal end of the obturator is closed off by an end wall, and the obturator being sized such that (i) when the trigger carriage is in the distal position, the distal end of the obturator extends beyond the sharp distal end of the needle, and (ii) when the trigger carriage is in the proximal position, the distal end of the obturator is received within the sharp distal end of the needle;
        a spring for urging the trigger carriage into the distal position;
        a trigger mounted to the trigger carriage for urging the trigger carriage towards the proximal position when operated;
        a first latch for releasably locking the trigger carriage in the distal position when the first latch is set, the latch configured to be set or released by operation of the trigger;
        a second latch for releasably locking the trigger carriage in an intermediate position located between the distal position and the proximal position, wherein the distal end of the obturator partially emerges from the hollow needle when the trigger carriage is in the intermediate position, the second latch configured to be set or released by operation of the trigger;
        the first latch, the second latch, and the trigger being configured so that when the trigger carriage is in its distal position and the first latch is set, and the trigger is thereafter pulled proximally, the first latch is released and the trigger carriage moves proximally into its proximal position, and thereafter releasing the trigger causes the trigger carriage to move into the intermediate position and set the second latch; and
        further wherein, when the trigger carriage is in its intermediate position and the distal end of the obturator engages tissue surrounding the hip joint, the trigger carriage is moved proximally so as to release the second latch;
    configuring the safety needle so that the trigger carriage is in the distal position and the first latch is set by operation of the trigger;
    moving the trigger so that the first latch is released and the trigger carriage moves proximally into the proximal position;
    releasing the trigger so as to cause the trigger carriage to move into the intermediate position and set the second latch; and
    advancing the safety needle so that the sharp distal end of the needle and the distal end of the obturator engage tissue surrounding the hip joint.

2. A method according to claim 1 wherein the hollow needle is releasably mounted to the handle.

3. A method according to claim 1 wherein the handle is hollow, and further wherein the trigger carriage is disposed within the handle.

4. A method according to claim 1 wherein the obturator is hollow and further wherein an opening is formed in the sidewall of the obturator just proximal to the end wall.

5. A method according to claim 1 wherein the obturator is releasably mounted to the trigger carriage.

6. A method according to claim 5 wherein the obturator is releasably mounted to the trigger carriage via a third latch.

7. A method according to claim 6 wherein the third latch comprises a finger for selectively engaging a notch formed in the obturator.

8. A method according to claim 1 wherein the spring is disposed between the trigger carriage and a release button, wherein the release button is slidably mounted to the handle, and further wherein the third latch is released when the release button is moved distally against the action of the spring.

9. A method according to claim 1 wherein the trigger is pivotally mounted to the trigger carriage.

10. A method according to claim 9 wherein the trigger comprises a finger-engaging portion, a distally-extending portion, and a proximally-extending portion.

11. A method according to claim 10 further comprising a second spring for biasing the finger-engaging portion of the trigger distally.

12. A method according to claim 10 wherein the first latch comprises the proximally-extending portion of the trigger.

13. A method according to claim 12 wherein the first latch is formed by engagement of the proximally-extending portion of the trigger with the handle.

14. A method according to claim 10 wherein the second latch comprises the distally-extending portion of the trigger.

15. A method according to claim 14 wherein the second latch is formed by engagement of the distally-extending portion of the trigger with the handle.

16. A method according to claim 1 wherein the handle comprises an internal chamber and a port for accessing the same, wherein the obturator extends through the internal chamber and comprises an opening in the sidewall of the obturator communicating with the internal chamber, and further wherein the handle comprises a sealing mechanism for engaging the obturator and preventing fluid from flowing out of the internal chamber about the periphery of the obturator.

17. A method according to claim 16 wherein the sealing mechanism is releasable so as to permit the obturator to be withdrawn from the internal chamber.

\* \* \* \* \*